(12) United States Patent
Mark

(10) Patent No.: US 6,673,031 B2
(45) Date of Patent: Jan. 6, 2004

(54) LIQUID APPLICATOR

(76) Inventor: Phillip Mark, 1255 LaQuinta Dr. #214A, Orlando, FL (US) 32809

( * ) Notice: Subject to any disclaimer, the term of this patent is extended or adjusted under 35 U.S.C. 154(b) by 91 days.

(21) Appl. No.: 09/960,960

(22) Filed: Sep. 25, 2001

(65) Prior Publication Data

US 2003/0060746 A1 Mar. 27, 2003

(51) Int. Cl.⁷ .............................................. A61M 35/00
(52) U.S. Cl. ................................................ 604/1; 604/2
(58) Field of Search .................. 604/1–3; 401/132–135, 401/196; 222/187

(56) References Cited

U.S. PATENT DOCUMENTS

| | | |
|---|---|---|
| 1,146,522 A | 7/1915 | Robert |
| 3,324,855 A | 6/1967 | Heimlich |
| 3,393,962 A | 7/1968 | Andrews |
| 3,757,782 A | 9/1973 | Aiken |
| 3,792,699 A | 2/1974 | Tobin et al. |
| 4,206,843 A | 6/1980 | Rainey |
| 4,415,288 A | 11/1983 | Gordon et al. |
| 4,507,111 A | 3/1985 | Gordon et al. |
| 4,572,689 A | 2/1986 | Chernack |
| 4,740,194 A | 4/1988 | Barabino et al. |
| 4,784,506 A | 11/1988 | Koreska et al. |
| 4,799,815 A | 1/1989 | Barabino et al. |
| 4,957,385 A | 9/1990 | Weinstein |
| 5,098,297 A | 3/1992 | Chari et al. |
| 5,100,028 A | 3/1992 | Seifert |
| 5,288,159 A | 2/1994 | Wirt |
| 5,308,180 A | 5/1994 | Pournoor et al. |
| 5,445,462 A | 8/1995 | Johnson et al. |
| 5,490,736 A | 2/1996 | Haber et al. |
| 5,538,353 A | 7/1996 | DeHavilland |
| 5,658,084 A | 8/1997 | Wirt |
| 5,738,634 A | 4/1998 | Caillouette |
| 5,772,346 A | 6/1998 | Edwards |
| 5,782,801 A | 7/1998 | Caillouette |
| 5,791,801 A | 8/1998 | Miller |
| 5,827,200 A | 10/1998 | Caillouette |
| 5,927,884 A | 7/1999 | Kao |
| 6,039,488 A | 3/2000 | Krawczyk et al. |
| 6,283,933 B1 * | 9/2001 | D'Alessio et al. |

* cited by examiner

*Primary Examiner*—Weilun Lo
*Assistant Examiner*—Jacqueline F Stephens
(74) *Attorney, Agent, or Firm*—Eric P. Schellin

(57) ABSTRACT

A liquid applicator includes an elongated hollowing body having opposed first and second open ends in fluid communication with one another, and a tip attached to the first open end and including a porous material. A closed, frangible ampule is supported within the second open end of the body and contains a liquid to be disposed.

1 Claim, 1 Drawing Sheet

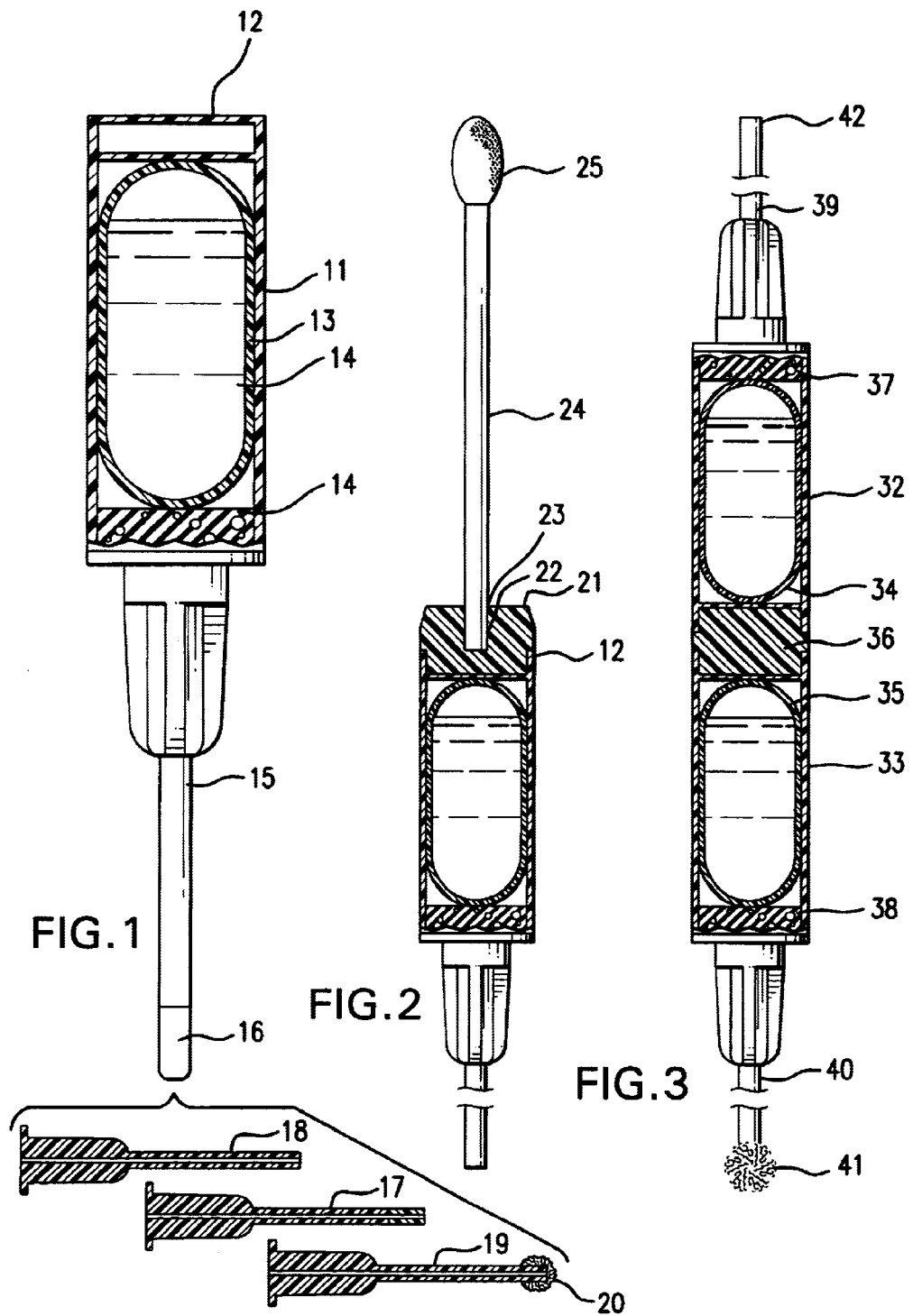

LIQUID APPLICATOR

BACKGROUND OF THE INVENTION

1. Field of the Invention

The present invention relates generally to liquid applicators and more particularly, to a disposable, self contained applicator having at least one ampule in which liquid is stored, and has a means for facturing the ampule to release the liquid for application.

2. Discussion of the Prior Art

It is known to provide a liquid applicator of generally cylindrical construction, including a glass ampule retained within the applicator, a swab, foam pad or tip exposed to the ampule, and a means for fracturing the ampule so that when the ampule is fractured, the liquid stored therein is dispensed to a egress conduit for application.

However, numerous problems are encountered with devices of this type. For example, known devices include either an unnecessarily large number of moving parts, which renders such devices expensive to construct as a disposable assembly, or require that a user employ both hands in breaking the ampule and dispensing the fluid.

In many situations, it is necessary for the user of a fluid dispenser of medicaments to use one hand to expose for positioning in the area of the body to be treated with the fluid while preparing the dispenser or use and applying the fluid with the other hand. Thus, it is very important for the user to be able to prepare and use the applicator with only one hand in order to enable the practical use thereof.

Another problem experienced with conventional applicators is that the pad used with many such applicators is useful only for applying a liquid over relatively large areas, without permitting a small volume of fluid to be accurately placed on a desired treatment location. It is known that where small amounts of fluid are to be applied at precise locations, a broken toothpick may be used in order to permit the fluid to be accurately placed without being inadvertently applied to surrounding areas.

Furthermore, there are patented applicators of this type such as the patent to Caillouette, U.S. Pat. No. 6,066,124 which is incorporated in its entirety by reference thereto.

OBJECTS AND SUMMARY OF THE INVENTION

It is an object of the present invention to provide a single-use, disposable liquid applicator which permits one-hand operation in order to free the other hand of the user for use in assisting with the applicator of fluid to a desired area.

It is another object of the present invention to provides a liquid applicator which permits the accurate placement of a very small and relatively closely controlled amount of a liquid on a treatment area without also permitting the liquid to spread to surrounding areas.

Yet another object of the present invention resides in the provision of a liquid applicator which is easy to use and which enables a user to visually inspect the liquid within the applicator in order to determine the amount of liquid therein, and to control the flow of liquid from the applicator.

In accordance with these and other objects evident from the following description of prepared embodiments of the invention, a liquid applicator includes an elongated hollow body having opposed first and second open ends in fluid communication with one another through the body, and a tip attached to the first open end of the body and including a porous material for allowing liquid within the body to be applied through the tip. A closed, frangible ampule is supported within the second open end of the body and contains a liquid to be dispensed.

In a second embodiment the end opposite the tip has attached thereto an axially extending elongated rod. The rod terminates in a cotton wads, for instance, so it can be used as a swab.

In still another major embodiment the hollow tubular body is supplied with two ampules separated by a plug mass. Each end of the tubular body has mounted axially thereon an applicator tip.

By constructing a liquid applicator in accordance with the present invention, numerous advantages are achieved. For example, by providing a relatively simple construction in which an ampule is stored within a body and is fractured at the time of use upon by inwardly compressing said body, an applicator is obtained which may be designed for single use, and which enables one-handed operation.

Further, by providing the liquid applicator with a means.

BRIEF DESCRIPTION OF THE DRAWINGS FIGURES

Preferred embodiments of the present invention is described in detail hereinafter with reference to the attached drawing figures, wherein:

FIG. 1 is an embodiment of the applicator of the present invention partially in cross-section and a cross section of various applicable tip embodiments.

FIG. 2 is second embodiment partial in cross section.

FIG. 3 is yet another embodiment partially in cross-section.

DETAILED DESCRIPTION

FIG. 1 is an elongated assembly which includes an upper hollow tubular body 11, preferably, of transparent plastic. The upper must end 12 is sealed. The hollow body 11 has a close fitting ampule 13 of glass which contains a medicament 14. The ampule 13 rests against an open celled foam disc 14 which is at the bottom at the hollow body 11. The foam disc 14 acts as a cushioning element inhibiting the breaking of the glass ampule 13.

The bottom of the hollow tubular body 11 is essentially open at the bottom thereof and is communication with an elongated conduit 15. The elongated conduit 15 terminates in one of the number of tips. The tip shown in FIG. 1 is an integrally injected molded foam plastic dabber 16, shown also in the various three embodiments by reference numeral 17. The embodiment shown by reference numeral 18 is of a simple and plain tip. In the embodiment shown by reference numeral 19 the tips ends with a ball of bristles 20.

FIG. 2 depicts another embodiment wherein the seal or top 12 has a plug 21 which has a recess 22. One end 23 of a swab 24 is adhesively secured thereinto. The distal end of the swab 24 terminates in a conventional cotton ball 25.

Then, in FIG. 3 an embodiment is shown wherein the hollow body 31 is more axially elongated. It is divided into an upper chamber 32 and a lower chamber 33. The upper chamber 32 has a relatively close fitting glass frangible ampule 34 and the lower chamber 33 has fitted therein a relatively close fitting frangible glow ampule 35. The two ampules 34 and 35 are separated by a wall or plug 36. The elongated tubular hollow body 31 is fitted at both ends with a sponge 37 and 38, respectfully. Fitted to both ends are conduit 39 and 40 of like type depicted with the embodiments shown in FIG. 1 and FIG. 2.

The conduit 40 terminates in bristles shaped in the form of a ball 41. While conduit 39 terminates in a plain top 42. It is contemplated that the conduits 39 and 40 may have any one of the three kinds of tips as discussed in conjunction with FIG. 1 in the foregoing.

In use of wall of the hollow tubular body is racially compressed to break the glass thereby releasing the liquid contained therein which migrates through the sponge and into the conduits 19, 39 or 40 for distribution out of the tip.

In FIG. 2, the liquid may be applied to a site. The applicator can then be reversed and the end carrying the swab or cotton ball may then be employed to distribute the applied liquid or to take a sample for testing.

In the FIG. 3 applicator embodiment, a first liquid may be applied to the site followed by the application of a second fluid to the same site to effect a reaction or the liquid may be applied to a different site.

The plug 36 constitutes a seal and is energy absorbing, such as an elastomeric material, and is designed to separate the ampules 34 and 35 sufficiently so that when one ampule is fractured the other ampule is not fractured due to proximity. The advantages is that a single structure of an applicator is presented without the danger that both ampules will be fractured when it is desired that only one is to be fractured.

The presence of the sponge prevents shards of glass from entering the respective conduits so acts as a filter.

It will be seen that the applicator of the present invention is easily assembled and requires a minimum of parts.

Although the invention has been described with reference to the preferred embodiment illustrated in the attached drawing figures, it is noted that substitutions may be made and equivalents employed herein without departing from the scope of the invention as recited in the claims.

What is claimed is:

1. A liquid applicator comprising:

a flexible elongated tubular hollow body having an opposed first and second open end;

said elongated tubular hollow body having in axial alignment two frangible ampules, said ampules each being filled with medicaments to be dispensed;

said ampules being axially physically separated from each other by a cylindrical plug;

said plug isolates said ampules from each other whereby when a wall of said hollow body proximate one ampule is compressed to shatter that particular ampule the other ampule is not simultaneously affected and shattered;

said first open end of said hollow body having a sponge disc;

said second open end of said hollow body having a sponge disc;

said first end having an axially extending first conduit having a distal end which termintes in a tip, said conduit adapted and constructed for liquid distribution therethrough from said hollow body and out of said tip;

said second end having an axially extending second conduit having a distal end which terminates in a tip, said conduit adapted and constructed for liquid distribution therethrough from said hollow body and out of said tip;

the first and second conduits are fabricated from an injection molded thermoplastic material and the said tip of each conduit is a distribution dauber;

at least one of said conduits and said tips are serially molded of thermoplastic materials having different physical properties whereby at least one of said conduits and said tips are integral.

* * * * *